United States Patent [19]

Eckelman et al.

[11] 4,431,627
[45] Feb. 14, 1984

[54] GAMMA-EMITTING RECEPTOR-BINDING 3-QUINUCLIDINYL GLYCOLATES; METHODS OF PREPARATION THEREOF AND IMAGING AND ASSAY METHODS UTILIZING SAME

[75] Inventors: William C. Eckelman, Rockville; Richard C. Reba, Silver Spring, both of Md.; Waclaw J. Rzeszotarski, Washington, D.C.; Raymond E. Gibson, Arlington, Va.

[73] Assignee: Research Corporation, New York, N.Y.

[21] Appl. No.: 336,340

[22] Filed: Dec. 31, 1981

Related U.S. Application Data

[63] Continuation-in-part of Ser. No. 156,106, Jun. 3, 1980, abandoned.

[51] Int. Cl.³ .............. A61K 49/00; A61K 43/00; C07D 453/02; G01N 33/54
[52] U.S. Cl. .......................... 424/1.1; 424/9; 436/542; 436/545; 546/137
[58] Field of Search .............. 546/137; 424/1, 9; 436/542, 545

[56] References Cited

U.S. PATENT DOCUMENTS

| | | | |
|---|---|---|---|
| 3,405,134 | 10/1968 | Judd | 546/137 |
| 3,714,357 | 1/1973 | Gueremy et al. | 546/137 |
| 3,833,592 | 9/1974 | Papanastassiou et al. | 546/137 |
| 3,910,929 | 10/1975 | Breslow | 546/137 |
| 4,017,596 | 4/1977 | Loberg et al. | 260/429 R |
| 4,082,756 | 4/1978 | Bauman | 546/137 |
| 4,360,511 | 11/1982 | Baldwin et al. | 424/1.5 |
| 4,363,793 | 12/1982 | Blau et al. | 424/1 |

FOREIGN PATENT DOCUMENTS

| | | | |
|---|---|---|---|
| 1800823 | 4/1969 | Fed. Rep. of Germany | 546/137 |
| 2640209 | 3/1977 | Fed. Rep. of Germany | 546/137 |
| 0725228 | 3/1955 | United Kingdom | 546/137 |

OTHER PUBLICATIONS

Proceedings of the First International Pharmacological Meeting, vol. 7, Ed. Brunings et al., Pergamon Press, N.Y. 1963, pp. 360–366.

*Primary Examiner*—Christine M. Nucker
*Attorney, Agent, or Firm*—Scully, Scott, Murphy & Presser

[57] ABSTRACT

Compounds of the formula:

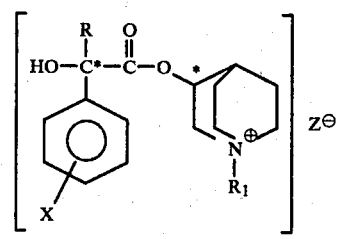

wherein
R is aryl, alkyl, cycloalkyl, phenyl, cyclopentyl, cyclohexyl, a ligand containing Tc-99m in chelated form or a ligand capable of chelating Tc-99m;
$R_1$ is H or lower alkyl;
X is in the ortho-, meta- or para- position, and is selected from the group consisting of $^{125}I$, $^{123}I$, $^{127}I$, I, $^{18}F$, $^{75}Br$, $^{77}Br$, $NH_2$, and

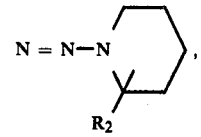

wherein $R_2$ is in the 2,3, or 4 position and is selected from the group consisting of H and lower alkyl, provided that when R is a ligand capable of chelating Tc-99m or containing Tc-99m in chelated form, X is not a radioisotope and may also be H or lower alkyl;
$Z^{\ominus}$ is an anion; or the free amine thereof; and * denotes an asymmetric carbon atom.

89 Claims, No Drawings

GAMMA-EMITTING RECEPTOR-BINDING 3-QUINUCLIDINYL GLYCOLATES; METHODS OF PREPARATION THEREOF AND IMAGING AND ASSAY METHODS UTILIZING SAME

RELATED APPLICATIONS

This application is a continuation-in-part of application Ser. No. 156,106, filed June 3, 1980, now abandoned.

BACKGROUND OF THE INVENTION

Field of the Invention

The present invention relates to various muscarinic cholinergic receptor-binding compounds, gamma-emitting radioisotope derivatives thereof, intermediate and methods for the production thereof and the use of the said radioisotope derivatives as radiopharmaceuticals in the assay and external imaging of myocardial tissue and other organs containing muscarinic cholinergic receptors.

It is known that muscarinic cholinergic receptors are concentrated in myocardial and other tissue. It is theorized that these receptors are involved in the action of drugs or biochemicals in the myocardial tissue and that changes in the concentration of the receptor in the myocardial tissue are a function of a disease state therein or in other tissue containing the receptors.

It has been established that various compounds function both in vitro and in vivo as muscarinic cholinergic receptor binders or antagonists. These compounds have a high affinity for and competitively bind with the receptor. It has been established that various 3-quinuclidinyl glycolates are effective muscarinic cholingergic receptor binders. It has further been suggested that tritium-labeled 3-quinuclidinyl glycolates may be utilized as radiotracers for various assay procedures involving myocardial tissue. See Eckelman et al, *J. Nucl. Med.*, 20, 350 (1979) and Gibson et al, *J. Nucl. Med.* 20, 865 (1979).

There are numerous disadvantages inherent in the use of tritium-labeled radiotracers. For example, numerous problems are associated with "counting" beta-emissions of tritium-labled compounds. Liquid scintillator must be added to each sample which is a time-consuming and expensive procedure. Toluene is the typical scintillator liquid employed which is presently subject to strict, environmental sanctions because it is not miscible with water thereby rendering its disposal problematical. In addition, beta-counting procedures are plagued with problems of chemluminescence and quenching which are absent in gamma-counting.

Tl-201 is presently employed for the detection and quantification of myocardial infarcts. However, the radiohalogens such as I-123 and Br-77 have better imaging characteristics in that their higher gamma energies can be detected with increased sensitivity and positional resolution as compared with the lower gamma energy of Tl-201 (80 Ke V X-rays).

Since the size of the infarct is related to mortality and residual function, improved resolution will mean improved prognosis and evaluation of drug therapy. The radiohalogens F-18 and Br-75 are positron emitters which offer the unique capabilities of resolution and quantification associated with such decay characteristics.

The unique radio imaging properties of Technetium-99m (Tc-99m) render radio imaging and radio assay agents containing the Tc-99m radioisotope more commercially viable than those agents containing other radioisotopes. Tc-99m has become the radioisotope of choice because:

(1) It has a six hour half-life thereby rendering it most efficient as an external imaging agent.

(2) Unlike other radioisotopes used as radio-tracers, there is no beta-component in the gamma-emission of Tc-99m.

(3) Technetium-99m is relatively inexpensive and widely available from molybdenum generators.

(4) There is a low absorbed radiation dose connected with the use of Tc-99m.

It is an object of the present invention to provide various 3-quinuclidinyl glycolates and gamma-emitting radioisotope containing 3-quinuclidinyl glycolates useful for muscarinic cholinergic receptor assays, and imaging of the myocardium and in vitro muscarinic cholinergic assay and tissue imaging techniques.

SUMMARY OF THE INVENTION

These and other objects of the present invention are achieved by providing compounds of the formula:

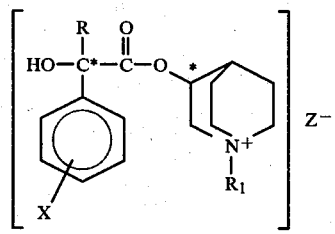

wherein

R is aryl (e.g., phenyl), alkyl, preferably lower alkyl, or cycloalkyl (e.g., cyclopentyl, cyclohexyl); a ligand containing Tc-99m in chelated form or a ligand capable of chelating Tc-99m;

$R_1$ is H or lower alkyl, preferably $CH_3$;

X is in the ortho-, meta- or para-position, and is selected from the group consisting of $^{125}I$, $^{123}I$, $^{127}I$, I, $^{18}F$, $^{75}Br$, $^{77}Br$, $NH_2$, H, lower alkyl, and

wherein $R_2$ is in the 2, 3, or 4 position and is selected from the group consisting of H and alkyl, provided that, when R is a ligand capable of chelating Tc-99m or contains Tc-99m in chelated form, X is H or lower alkyl; and n=3, 4, 5 or 6;

$Z^{\ominus}$ is an anion; or the corresponding free amine, i.e., the non-protonated or non-quaternary salt form; and

*denotes an asymmetric carbon atom.

The radio-labeled compounds are gamma-emitting and are useful in formulating compositions suitable for in vitro assay of muscarinic cholinergic receptors in, e.g., myocardial tissue and for formulating compositions suitable for use in external imaging or radio-assay of myocardial tissue and other tissues containing muscarinic cholinergic receptors.

The derivatives wherein X is H, lower alkyl, halogen, amino- and triazeno- are valuable as intermediates in the preparation of the radio-labeled analogs.

DETAILED DESCRIPTION OF THE INVENTION

The 4-aminobenzil may be prepared according to the method of Augl et al, *Annu. Conf.*, SPE, Reinf. Plastic/Compos. Div. Proc., 26th, 19D, 1 (1971). The 4-aminobenzil is rearranged to yield 4-aminobenzilic acid which is in turn esterfied to produce the ethyl ester. The ethyl ester of the 4-aminobenzilic acid is then reacted with quinuclidin-3-ol to give the expected 3-quinuclidinyl 4-aminobenzilate (4-amino-QNB). The purified 4-amino-QNB is then converted to the 4-triazeno-QNB according to the procedure reported by Tewson et al, *J. Nucl. Med.* 20, 671 (1979). The purified 4-triazeno-QNB is then reacted with iodide or a desired gamma-emitting radionuclide to produce the desired product.

In the above structural formula the anion $Z^\ominus$ may be any pharmaceutically acceptable anion such as $Cl^-$, $Br^-$, or $I^-$, $SO_4^=$, $HCOO^-$, $CH_3COO^-$, etc.

The compounds of the invention each possess two asymmetric carbon atoms in the quinuclidinyl glycolate moiety. It has been found that the activity of the compounds as muscarinic cholinergic receptor-binders depends upon the absolute configuration of the C* atoms in the above structural formula. Although the S, S; R, S and S, R-isomers and the racemic diastereomeric mixture are active, the R, R configuration is more highly active in most instances. Accordingly, it is preferred to utilize the R, R-isomer (i.e., at the C* atoms in the above structured formula) in the invention described herein.

The following examples illustrate the preparation of the claimed compounds.

EXAMPLE 1

4-Aminobenzilic Acid

A solution of 25 g of NaOH in 50 ml of $H_2O$ was placed in a water bath kept at 95° C. To this magnetically stirred solution was added 11.26 g (50 mmol) of 4-aminobenzil in small portions. After the addition was completed the mixture was stirred for 5 hours at 95° C. Water was added during the reaction to maintain the volume at about 100 ml. After 5 hours the heating was discontinued and the reaction mixture was transferred to a separatory funnel and extracted twice with 50 ml of ethyl ether. The aqueous layer was cooled to 0° acidified with conc. $H_2SO_4$ until turbid, and extracted with ethyl acetate (AcOEt) (100 ml). The aqueous layer was acidified and extracted with AcOEt again. The combined AcOEt layers were washed with water (2×), dried over $MgSO_4$, filtered and spin evaporated in vacuum. Thus obtained precipitate was recrystallized from water/acetone 25/75. Yield 8.9 g (73%). Yellow crystals, mp dec. 150° C.; Silica gel TLC in acetone, Rf 0.25; HPLC Bondapak $\mu C_{18}$ in $MeOH/H_2O$ (75/25) pH 4 (formic acid). IR, UV, mass spec. were consistent with the structure. Elemental Analysis calc for $C_{14}H_{13}NO_3.2/3\ H_2O$, calc. C 67.28, H 5.78, N 5.60; Found C 67.45, 67.64, H 5.49, 5.41, N 5.52, 5.51.

EXAMPLE 2

4-Aminobenzilic Acid Ethyl Ester 4.8 g (19.7 mmol) of 4-aminobenzilic acid was dissolved in 200 ml of absolute ethanol (EtOH) saturated with dry HCl gas. The reaction mixture was refluxed for 24 hours then spin evaporated to dryness in vacuum. The residue was dissolved in water and neutralized with $NaHCO_3$, extracted with 2×50 ml of AcOEt, washed with water (2×) and the AcOEt extract filtered through a siliconized filter and dried over $MgSO_4$. The dried solution was filtered and spin evaporated in vacuum. Yellow oil, 2.8 g (52%). SGTLC in acetone Rf 0.8. HPLC Bondapak $\mu C_{18}$ $MeOH/H_2O$ (75:25) pH 4 (formic acid). Elemental Analysis Calc. for $C_{16}H_{17}NO_3$. Calc. C 70.83, H 6.32, N 5.16; Found C 70.77, H 6.47, N 5.04, 5.26.

EXAMPLE 3

4-Aminobenzilate of 3-(R,S)-quinuclidinol 5.16 g (40 mmol) of 3-(R,S)-quinuclidinol was dissolved in 50 ml of dry benzene and 20 ml of benzene distilled off. A clean 100 mg piece of sodium was added and the suspension magnetically stirred, protected from moisture and $CO_2$ (NaOH trap), and refluxed for 24 hours. 2.8 g (10.3 mmol) of ethyl 4-aminobenzilate was dissolved in 50 ml of dry benzene and 20 ml of benzene removed by distillation.

Both solutions were combined and refluxed, protected from moisture and $CO_2$ for 24 hours. The solution was spin evaporated, the residue suspended in water and extracted twice with 50 ml of AcOEt. The AcOEt extract was washed repeatedly with water, filtered through a siliconized filter paper and dried over $MgSO_4$. The dried solution was filtered and spin evaporated in vacuum. The residue was dissolved in $CH_3CN$ and charged on a silica gel column (2.8×100 cm) eluted with $CH_3CN$. Pure fractions crystallized on standing. The product recrystallized from $CH_3CN$, 1.5 g (41%) white crystals; SGTLC n-butanol, acetic acid, water 4:1:1, Rf 0.4; HPLC Bondapak $\mu C_{18}$ $MeOH/H_2O$ 40/60, pH 4 (formic acid). IR, UV, mass spec. were consistent with the structure of the product. Calc. for $C_{21}H_{24}N_2O_3$. Calc. C 71.57, H 6.86, N 7.95; Found C 71.27, H 6.87, N 8.19.

EXAMPLE 4

4-[2-(3-methylpiperid-1-yl)-1,2-diaza-ethylen-1-yl]-benzilate of 3-(R,S)-quinuclidinol Sodium nitrite (75 mg, 1.08 mmol) was added to a cooled (0° C.) solution of 190 mg (54 mmol) of 4-amino-QNB in 6 ml of 10% H SO and acetone (5:1). The mixture was stirred for 15 min. at 0° then treated with 65 mg (1.08 mmol) of urea.

The diazonimum salt slurry was added to a cooled (0° C.) solution of 536 mg (5.4 mmol) of 3-methylpiperidine in 5 ml of water. The mixture was stirred at 0° C. for 20 min. then made basic with 4 N NaOH to pH 12 and extracted with $CHCl_3$ (3×5 ml). The combined extracts were washed repeatedly with water and dried over $MgSO_4$. The solution was filtered and spin evaporated in vacuum. The residue was extracted with petroleum ether (3×10 ml) and the combined extracts evaporated and dried in high vacuum to remove the traces of 3-methylpiperidine. Obtained was 240 mg (96%) of viscous yellow oil. SGTLC in 2% $NH_4OH$ in MeOH, Rf 0.5. HPLC Bondapak $\mu C_{18}$ 5 mM 1-hexanesulfonic acid pH 4 ($H_2SO_4$) in MeOH/H O, 60/40. UV, IR, mass spec. were consistent with the product structure. Elemental analysis for $C_{27}H_{34}N_4O_3.2H_2O$. Calc. 65.03, H 7.68, N 11.23; Found C 65.35, H 7.44, N 10.62.

EXAMPLE 5

(R,S)-Quinuclidin-3-ol-4-iodobenzilate

A solution of 5 mg (11 μmol) of QNB-triazene and 1.6 mg (11 μmol) of sodium iodide in 1 ml of trifluoroethanol was treated with 6.4 mg of methanesulfonic acid. The reaction mixture was heated on a water bath for 45 min., cooled, 5 ml of water added and extracted with 2×5 ml of AcOEt. The aqueous layer was then neutralized with 4 N NaOH and extracted with 3×5 ml of AcOEt. The organic layer was washed three times with 1 ml of water, filtered through a siliconized paper and dried over $Na_2SO_4$. After spin evaporation in vacuum, a yield of 2.7 mg (54%) was obtained as a yellow oil. UV, IR, mass spec. were consistent with the product structure. SGTLC in n-BuOH:AcOH:H O, 4:1:1, Bondapak $\mu C_{18}$ 5 mM 1-octanesulfonic acid, pH 4, MeOH/$H_2O$, 60/40.

EXAMPLE 6

(R,S)-Quinuclidin-3-ol-4-bromo or 4-iodo or 4-fluorobenzilate (radio nuclides)

The compounds are prepared using the above procedure to produce the iodobenzilate substituting sodium radioiodide or radiobromide or tetrabutyl ammonium radiofluoride for sodium iodide.

To prepare the protonated or quaternary derivative, the product of Example 5 or 6 is dissolved in a solution of the appropriate salt or alkyl halide and recrystallized therefrom.

EXAMPLE 7

The radiohalogen containing compound is utilized for imaging as follows:

The radio labeled tracer (I-123-QNB) is injected intravenously in the amount of 1 to 10 mCi at a specific activity to exceed 1000 Ci/mmol. Images of the distribution of radioactivity in the target organ are obtained as a function of time and the data stored in a computer. The data is then analyzed using an appropriate pharmacokinetic model to determine the concentration of receptors as a function of disease. Alternately, the information can be used to determine the blood flow to the target organ. For positron-emitting radiotracers such as Br-75 and F-18, coincidence counting is used. The images are collected over 2 hours and the target organ can be any locus of muscarinic cholinergic receptors such as the brain, the heart or the pancreas.

EXAMPLE 8

The radiohalogen containing compound can be used for the radio assay of tissue as follows:

Heart microsomal preparations are obtained as described by Harden et al [Mol Pharmacol 12: 1-15, 1976]. The heart from a rabbit is removed after the animal has been killed by cervical dislocation under light ether anesthesia. The heart is dissected free from atria and large vessels, minced with scissors and homogenized in buffer using a Brinkman Polytron. The homogenate is centrifuged at 10,000 g for 20 min. and the supernatent discarded. The pellet is resuspended in buffer and recentrifuged. The pellet is then suspended in buffer. This homegenate is centrifuged over a layer of 0.2 M sucrose above a layer of 1.72 M sucrose. Membranes are collected at the interface of the two sucrose layers and used immediately for the radio-receptor assay.

Aliquots of the muscarinic cholinergic receptor isolated above, I-125 IQNB and the test drugs are incubated at 37° C. with agitation. Incubations are carried out routinely for 120 min. Each incubation is terminated within 10 sec. by filtering the suspension through a GF/C glass fiber filter positioned over a vacuum flask. The filter is rinsed with 10 ml of buffer. The filter is then counted in a NaI(Tl) scintillation counter. Specific binding is experimentally determined from the difference between counts bound in the absence and presence of 1 μM atropine.

This same procedure can be used for any of the radiohalide-labeled derivatives of the invention.

The preferred technetium 99m (Tc-99m) derivatives may be prepared by synthesis of a 3-quinuclidinyl glycolate with a ligand capable of chelating Tc-99m to form an intermediate chelating agent and subsequently labeling the intermediate with Tc-99m by chelation.

Any chelating agent capable of forming the quinuclidinyl glycolate may be utilized provided that the resulting intermediate product is (1) capable of chelating Tc-99m and that (2) the Tc-99m labeled compound retains its muscarinic cholinergic receptor binding properties.

Preferred agents are those primary and secondary amine groups containing ligands capable of reaction through the amino group thereof with an ethynyl derivative of 3-quinuclidinyl glycolate via the Mannich reaction to yield the intermediate chelating agent. Exemplary of such amines are the so-called macrocyclic amines such as cyclam [1,4,8,11-tetraazacyclotetradecane] or its derivatives and kethoxal-bis (thiosemicarbazone) (KTS).

The intermediate chelating agent is prepared according to the following reaction scheme:

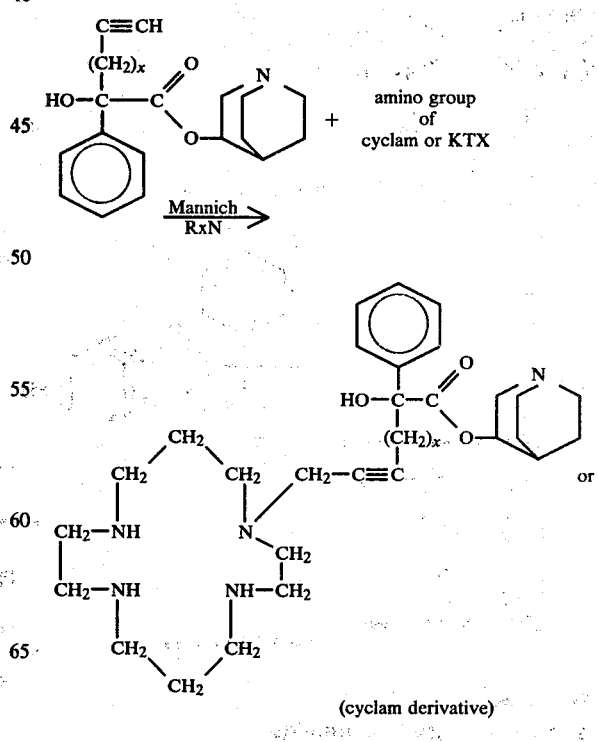

(cyclam derivative)

-continued

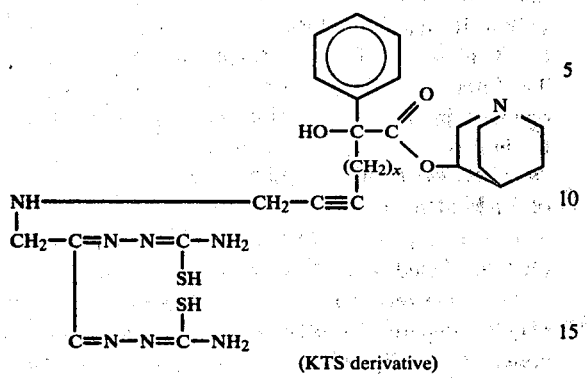

(KTS derivative)

The value of x is not critical and may range from about one to about ten.

The resulting intermediates are labeled with Tc-99m according to standard chelating procedures utilizing the pertechnetate (i.e., $^{99m}TcO_4^-$) and a suitable reducing agent. [Troutner et al, J. Nucl. Med. 21: 443–448, 1980 and Yokoyama et al, J. Nucl. Med. 17: 816–819, 1976].

The resulting 99m-Tc labeled derivatives have the following structural formulas:

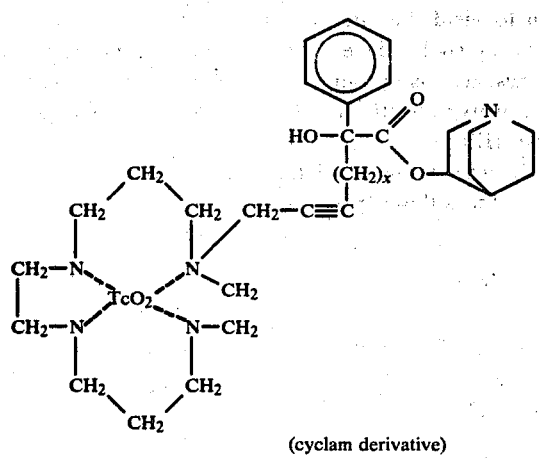

(cyclam derivative)

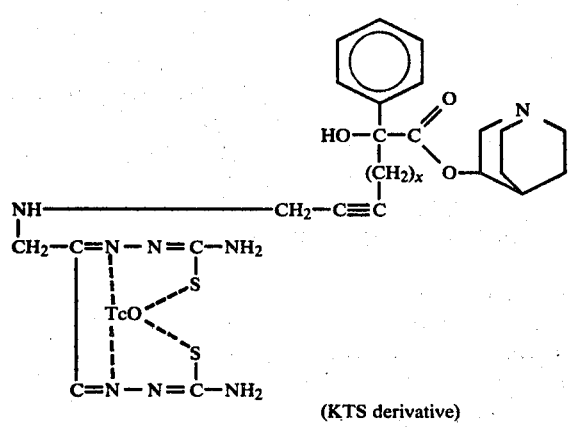

(KTS derivative)

We claim:
1. A compound of the formula:

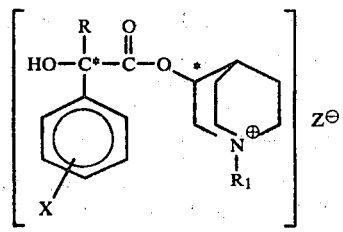

wherein
R is aryl, alkyl, cycloalkyl, phenyl, cyclopentyl, cyclohexyl, a ligand containing Tc-99m in chelated form or a ligand capable of chelating Tc-99m;
$R_1$ is H or lower alkyl;
X is in the ortho-, meta- or para-position, and is selected from the group consisting of $^{125}I$, $^{123}I$, $^{127}I$, I, $^{18}F$, $^{75}Br$, $^{77}Br$, $NH_2$, and

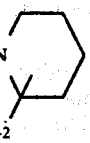

wherein $R_2$ is in the 2, 3, or 4 position and is selected from the group consisting of H and lower alkyl, provided that when R is a ligand capable of chelating Tc-99m or containing Tc-99m in chelated form, X is not a radioisotope and may also be H or lower alkyl;
$Z^\ominus$ is an anion; or the free amine thereof; and
*denotes an asymmetric carbon atom.

2. A compound according to claim 1 of the formula:

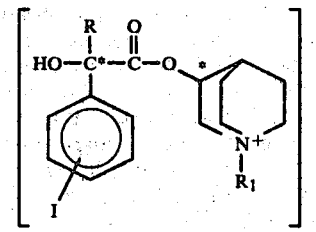

wherein
R is phenyl, cyclopentyl or cyclohexyl,
$R_1$ is H or $CH_3$,
I is in the ortho-, meta- or para-position, and
$Z^\ominus$ is an anion; or the free amine form thereof.

3. The compound of claim 2 wherein said I is in the meta-position and $R_1$ is H.
4. The compound of claim 2 wherein said I is in the meta-position and $R_1$ is $CH_3$.
5. The compound of claim 2 wherein said I is in the para-position and $R_1$ is H.
6. The compound of claim 2 wherein said I is in the para-position and $R_1$ is $CH_3$.
7. The compound of claim 2 wherein said I is in the ortho-position and $R_1$ is H.
8. The compound of claim 2 wherein said I is in the ortho-position and $R_1$ is $CH_3$.
9. A compound according to claim 1 of the formula:

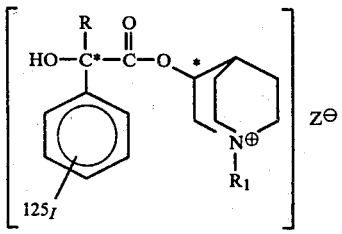

wherein

R is phenyl, cyclopentyl or cyclohexyl,
$R_1$ is H or $CH_3$,
$^{125}I$ is in the ortho-, meta- or para-position, and
$Z^\ominus$ is an anion; or the free amine form thereof.

10. The compound of claim 9 wherein said $^{125}I$ is in the meta-position and $R_1$ is H.

11. The compound of claim 9 wherein said $^{125}I$ is in the meta-position and $R_1$ is $CH_3$.

12. The compound of claim 9 wherein said $^{125}I$ is in the para-position and $R_1$ is H.

13. The compound of claim 9 wherein said $^{125}I$ is in the para-position and $R_1$ is $CH_3$.

14. The compound of claim 9 wherein said $^{125}I$ is in the ortho-position and $R_1$ is H.

15. The compound of claim 9 wherein said $^{125}I$ is in the ortho-position and $R_1$ is $CH_3$.

16. A compound according to claim 1 of the formula:

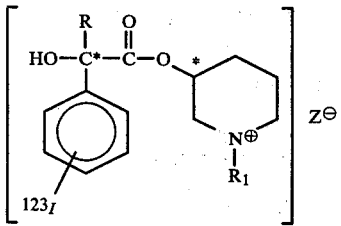

wherein

R is phenyl, cyclopentyl or cyclohexyl,
$R_1$ is H or $CH_3$,
$^{123}I$ is in the ortho-, meta- or para-position, and
$Z^\ominus$ is an anion; or the free amine form thereof.

17. The compound of claim 16 wherein said $^{123}I$ is in the meta-position and $R_1$ is H.

18. The compound of claim 16 wherein said $^{123}I$ is in the meta-position and $R_1$ is $CH_3$.

19. The compound of claim 16 wherein said $^{123}I$ is in the para-position and $R_1$ is H.

20. The compound of claim 16 wherein said $^{123}I$ is in the para-position and $R_1$ is $CH_3$.

21. The compound of claim 16 wherein said $^{123}I$ is in the ortho-position and $R_1$ is H.

22. The compound of claim 16 wherein said $^{123}I$ is in the ortho-position and $R_1$ is $CH_3$.

23. A compound according to claim 1 of the formula:

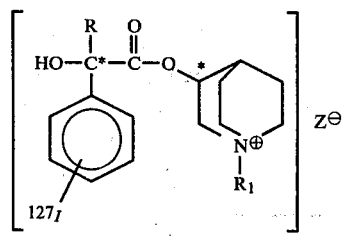

wherein

R is phenyl, cyclopentyl or cyclohexyl,
$R_1$ is H or $CH_3$,
$^{127}I$ is in the ortho-, meta- or para-position, and
$Z^\ominus$ is an anion; or the free amine form thereof.

24. The compound of claim 23 wherein said $^{127}I$ is in the meta-position and $R_1$ is H.

25. The compound of claim 23 wherein said $^{127}I$ is in the meta-position and $R_1$ is $CH_3$.

26. The compound of claim 23 wherein said $^{127}I$ is in the para-position and $R_1$ is H.

27. The compound of claim 23 wherein said $^{127}I$ is in the para-position and $R_1$ is $CH_3$.

28. The compound of claim 23 wherein said $^{127}I$ is in the ortho-position and $R_1$ is H.

29. The compound of claim 23 wherein said $^{127}I$ is in the ortho-position and $R_1$ is $CH_3$.

30. A compound according to claim 1 of the formula:

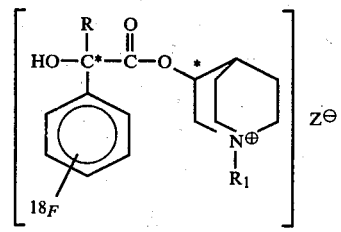

wherein

R is phenyl, cyclopentyl or cyclohexyl,
$R_1$ is H or $CH_3$,
$^{18}F$ is in the ortho-, meta- or para-position, and
$Z^\ominus$ is an anion; or the free amine form thereof.

31. The compound of claim 30 wherein said $^{18}F$ is in the meta-position and $R_1$ is H.

32. The compound of claim 30 wherein said $^{18}F$ is in the meta-position and $R_1$ is $CH_3$.

33. The compound of claim 30 wherein said $^{18}F$ is in the para-position and $R_1$ is H.

34. The compound of claim 30 wherein said $^{18}F$ is in the para-position and $R_1$ is $CH_3$.

35. The compound of claim 30 wherein said $^{18}F$ is in the ortho-position and $R_1$ is H.

36. The compound of claim 30 wherein said $^{18}F$ is in the ortho-position and $R_1$ is $CH_3$.

37. A compound according to claim 1 of the formula:

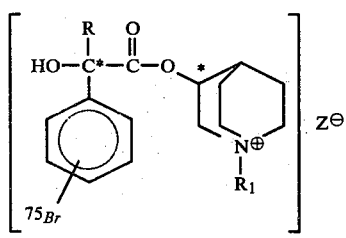

wherein
R is phenyl, cyclopentyl, or cyclohexyl,
$R_1$ is H or $CH_3$,
$^{75}Br$ is in the ortho-, meta- or para-position, and
$Z^\ominus$ is an anion; or the free amine form thereof.

38. The compound of claim 37 wherein said $^{75}Br$ is in the meta-position and $R_1$ is H.

39. The compound of claim 37 wherein said $^{75}Br$ is in the meta-position and $R_1$ is $CH_3$.

40. The compound of claim 37 wherein said $^{75}Br$ is in the para-position and $R_1$ is H.

41. The compound of claim 37 wherein said $^{75}Br$ is in the para-position and $R_1$ is $CH_3$.

42. The compound of claim 37 wherein said $^{75}Br$ is in the ortho-position and $R_1$ is H.

43. The compound of claim 37 wherein said $^{75}Br$ is in the ortho-position and $R_1$ is $CH_3$.

44. A compound according to claim 1 of the formula:

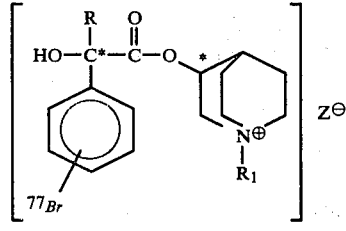

wherein
R is phenyl, cyclopentyl or cyclohexyl,
$R_1$ is H or $CH_3$
$^{77}Br$ is in the ortho-, meta- or para-position, and
$Z^\ominus$ is an anion; or the free amine form thereof.

45. The compound of claim 44 wherein said $^{77}Br$ is in the meta-position and $R_1$ is H.

46. The compound of claim 44 wherein said $^{77}Br$ is in the meta-position and $R_1$ is $CH_3$.

47. The compound of claim 44 wherein said $^{77}Br$ is in the para-position and $R_1$ is H.

48. The compound of claim 44 wherein said $^{77}Br$ is in the para-position and $R_1$ is $CH_3$.

49. The compound of claim 44 wherein said $^{77}Br$ is in the ortho-position and $R_1$ is H.

50. The compound of claim 44 wherein said $^{77}Br$ is in the ortho-position and $R_1$ is $CH_3$.

51. A compound according to claim 1 of the formula:

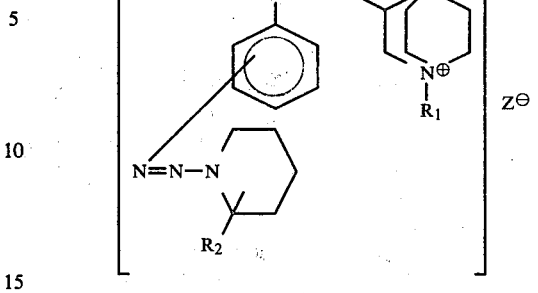

wherein
R is phenyl, cyclopentyl or cyclohexyl,
$R_1$ is H or $CH_3$, the triazene group is in the ortho-, meta- or para-position,
$R_2$ is H or lower alkyl in the 2, 3, or 4 position, and
$Z^\ominus$ is an anion; or the free amine form thereof.

52. The compound of claim 51 wherein said triazene group is in the meta-position and $R_1$ is H.

53. The compound of claim 51 wherein said triazene group is in the meta-position and $R_1$ is $CH_3$.

54. The compound of claim 51 wherein said triazene group is in the para-position and $R_1$ is H.

55. The compound of claim 51 wherein said triazene group is in the para-position and $R_1$ is $CH_3$.

56. The compound of claim 51 wherein said triazene group is in the ortho-position and $R_1$ is H.

57. The compound of claim 51 wherein said triazene group is in the ortho-position and $R_1$ is $CH_3$.

58. A compound according to claim 1 of the formula:

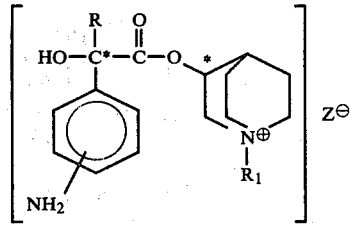

wherein
R is phenyl, cyclopentyl or cyclohexyl,
$R_1$ is H or $CH_3$,
$NH_2$ is in the ortho-, meta- or para-position, and
$Z^\ominus$ is an anion; or the free amine form thereof.

59. The compound of claim 55 wherein said $NH_2$ is in the meta-position and $R_1$ is H.

60. The compound of claim 58 wherein said $NH_2$ is in the meta-position and $R_1$ is $CH_3$.

61. The compound of claim 58 wherein said $NH_2$ is in the para-position and $R_1$ is H.

62. The compound of claim 58 wherein said $NH_2$ is in the para-position and $R_1$ is $CH_3$.

63. The compound of claim 58 wherein said $NH_2$ is in the ortho-position and $R_1$ is H.

64. The compound of claim 58 wherein said $NH_2$ is in the ortho-position and $R_1$ is $CH_3$.

65. A method of preparing a compound of claim 58 comprising reacting a derivative of an aminobenzilic acid with a quinuclidin-3-ol to produce a quinuclidinyl aminobenzilate.

66. A method for preparing a compound of claim 51 comprising reacting a derivative of an aminobenzilic acid with a quinuclidin-3-ol to produce a quinuclidinyl aminobenzilate and converting the free amine group to a triazene group.

67. A method for preparing a compound of claim 1 comprising reacting a derivative of an aminobenzilic acid with a quinuclidin-3-ol to produce a quinuclidinyl aminobenzilate, converting the free amino group to a triazene group, reacting the triazene derivative with a halogenide or radiohalogenide to form 3-quinuclidinyl halo benzilate.

68. A composition suitable for the assay of muscarinic cholinergic receptors in tissue comprising a gamma-emitting radioisotope containing compound of claim 1 and a pharmaceutically acceptable carrier therefor.

69. A composition of claim 68 wherein said gamma-emitter is $^{125}$I.

70. The composition of claim 68 wherein said gamma-emitter is $^{123}$I.

71. The composition of claim 68 wherein said gamma-emitter is $^{127}$I.

72. The composition of claim 68 wherein said gamma-emitter is $^{18}$F.

73. The composition of claim 68 wherein said gamma-emitter is $^{75}$Br.

74. The composition of claim 68 wherein said gamma-emitter is $^{77}$Br.

75. The composition of claim 68 wherein said gamma-emitter is Tc-99m.

76. A composition in unit dosage form suitable for use in a method for the external imaging or radio-assay of tissue containing muscarinic cholinergic receptors comprising a gamma-emitting radioisotope containing compound of claim 1 and a pharmaceutically acceptable carrier therefor.

77. In a method for the external imaging of or the radio-assay of muscarinic cholinergic receptors in tissue wherein a composition comprising a gamma-emitting radio-isotope containing muscarinic cholinergic receptor binding compound is administered to an animal or human patient and the gamma-emissions from the receptor-bound radio-isotope containing compound are converted to visible images of the tissue or are otherwise quantitatively analyzed to determine muscarinic cholinergic receptor concentration in said tissue, the improvement wherein said administered compound is a gamma-emitting radioisotope containing compound of claim 1.

78. The method of claim 77 wherein said gamma-emitter is $^{123}$I.

79. The method of claim 77 wherein said gamma-emitter is $^{125}$I.

80. The method of claim 80 wherein said gamma-emitter is $^{127}$I.

81. The method of claim 77 wherein said gamma-emitter is $^{18}$F.

82. The method of claim 77 wherein said gamma-emitter is $^{75}$Br.

83. The method of claim 77 wherein said gamma-emitter is $^{77}$Br.

84. The method of claim 77 wherein said gamma-emitter is Tc-99m.

85. A compound according to claim 1 of the formula:

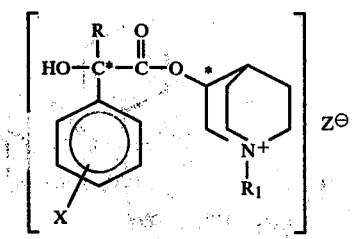

wherein

R is a ligand containing technetium-99m in chelated form or a ligand capable of chelating Tc-99m;

$R_1$ is H or lower alkyl,

X is in the ortho-, meta- or para-position and is either H or lower alkyl, and $Z^\ominus$ is an anion, or the free amine form thereof.

86. A compound according to claim 1 having the formula:

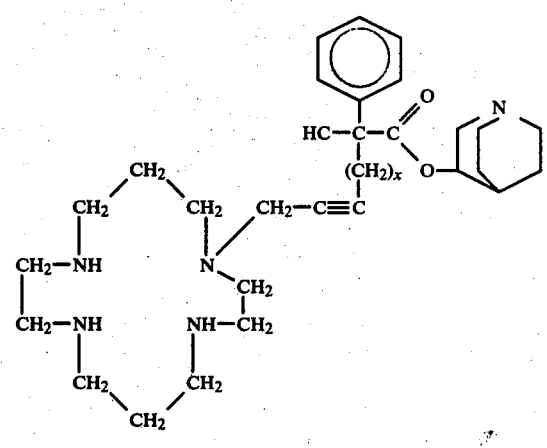

wherein x=one to ten.

87. A compound according to claim 1 having the formula:

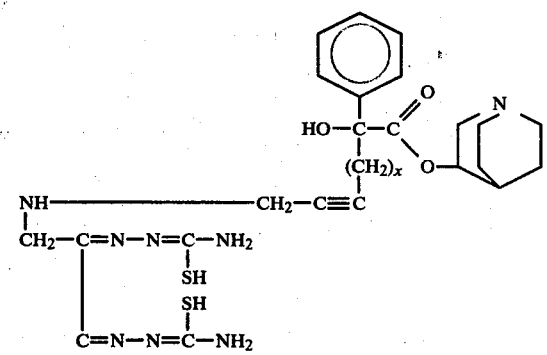

wherein x=one to ten.

88. A compound according to claim 1 having the formula:

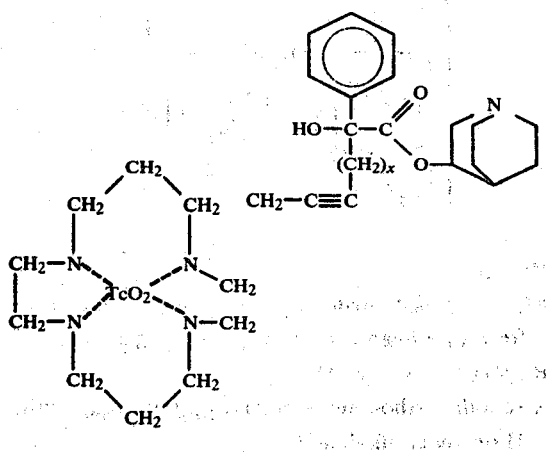
wherein x=one to ten, and Tc is Tc-99m.
89. A compound according to claim 1 having the formula:
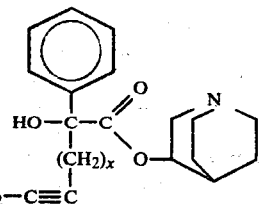
wherein x=one to ten, and Tc is Tc-99m.
* * * * *